(12) United States Patent
Jensen et al.

(10) Patent No.: US 6,248,090 B1
(45) Date of Patent: Jun. 19, 2001

(54) SYRINGE WITH ELECTRONIC REPRESENTATION OF PARAMETERS

(75) Inventors: Jens Moller Jensen, Copenhagen K; Jens Ulrik Poulsen, Virum; Jorgen K. Smedegaard, Frederiksberg, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/137,014

(22) Filed: Aug. 20, 1998

(30) Foreign Application Priority Data

Feb. 23, 1996 (DK) .................................................... 0199/96

(51) Int. Cl.[7] .................................................. A61M 31/00
(52) U.S. Cl. ............................................... 604/67; 604/207
(58) Field of Search ...................................... 604/128, 154, 604/207, 208, 209, 210, 211, 65, 66, 67, 120, 121, 186; 368/10

(56) References Cited

U.S. PATENT DOCUMENTS

| | | | |
|---|---|---|---|
| 3,871,361 | * 3/1975 | Kamen | 128/213 |
| 4,275,727 | 6/1981 | Keeri-Szanto . | |
| 4,529,401 | * 7/1985 | Leslie et al. | 604/131 |
| 4,662,872 | * 5/1987 | Cane | 604/151 |
| 4,735,619 | * 4/1988 | Sperry et al. | 604/208 |
| 4,776,842 | * 10/1988 | Franetzki et al. | 604/67 |
| 4,893,291 | 1/1990 | Bick et al. . | |
| 4,950,246 | * 8/1990 | Muller | 604/154 |
| 5,100,380 | * 3/1992 | Epstein et al. | 604/67 |
| 5,215,523 | * 6/1993 | Williams et al. | 604/97 |
| 5,236,416 | * 8/1993 | McDaniel et al. | 604/67 |

FOREIGN PATENT DOCUMENTS

| | | |
|---|---|---|
| 0 362 484 | 4/1990 | (EP) . |
| WO 95/24233 | 9/1995 | (WO) . |

* cited by examiner

*Primary Examiner*—Manuel Mendez
(74) *Attorney, Agent, or Firm*—Steve T. Zelson, Esq.

(57) ABSTRACT

A syringe having a dose setting mechanism, a button which can be operated to inject a set dose, a switch operated at a time between the start and completion of injection, and an electronic presentation of parameters such as the size of a set dose and the size of the last dose administered. The syringe also has a stop watch which is reset and started responsive to operation of the switch. The electronic presentation includes an indication of the number of hours elapsed from the activation of the switch, and may also include, for a predetermined period initially following the activation of the switch, a presentation of the number of seconds elapsed. The latter presentation can provide a visual indication to the patient of the length of time, after the injection button has been actuated to inject the dose, that the needle should remain inserted in the skin.

12 Claims, 2 Drawing Sheets

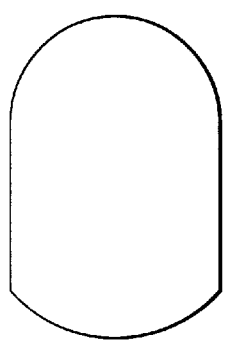
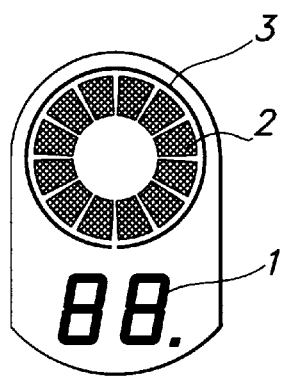
FIG 1     FIG 2
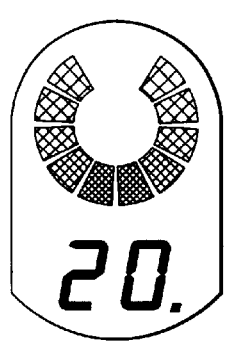
FIG 3     FIG 4
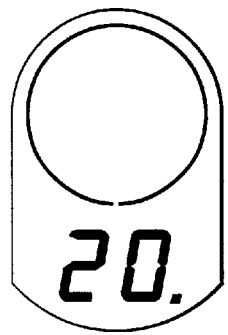
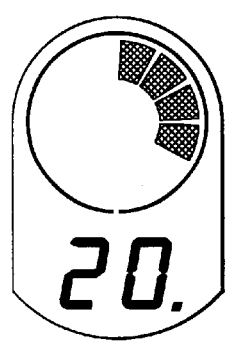
FIG 5     FIG 6

SYRINGE WITH ELECTRONIC REPRESENTATION OF PARAMETERS

CROSS-REFERENCE TO RELATED APPLICATIONS

This application is a 35 U.S.C. 371 national application of PCT/DK97/00077 filed Feb. 20, 1997 and claims priority under 35 U.S.C. 119 of Danish application 0199/96 filed Feb. 23, 1996, the contents of which are fully incorporated herein by reference.

STATEMENT REGARDING FEDERALLY SPONSORED RESEARCH OR DEVELOPMENT

Not Applicable

BACKGROUND OF THE INVENTION

The invention relates to syringes of the type having a dose setting mechanism, a button operable to carry out an injection movement to inject the set dose, a switch operated when an injection is made at the start or at the completion of this injection, or at a time between the start and the completion of this injection, and an electronic representation of relevant parameters such as of a set dose and the latest injected dose.

The electronic representation usually is in the form of an electronic display showing numbers indicating the numbers of international units of the medicament in the set and the latest injected dose. However, to show consideration to visually impaired people the electronic representation may be effected by a speech circuit which announces the numbers rather than displaying them. Alternatively the numbers may also by electronic or electromechanical means be transformed into a tactile code, or the numbers may be communicated through a suitable interface for presentation by any external means, e.g. TV screens, PC monitors etc.

Diabetics who have to frequently inject themselves with insulin may wish to know not only the magnitude of the latest injected dose but also how long time has passed since the latest injection was made.

EP 87 491 discloses a kit comprising a storage box for insulin vials and a syringe which kit is provided with a timer device by which the time for the latest injection may be set manually. Further the hour for the next injection may be set and the timing device may function as an alarm clock sounding an alarm when it is time for this next injection. However, in a world where people may in a short time cross from one time zone to another, and the hours in the time zones even may shift from summer to winter time, a reference to the hour is uncertain. Here the count down is more adequate but has the drawback that unless you are ready to take an injection immediately when the alarm sounds you will have a new time account to handle, e.g. for how long an interval was the alarm set and how long time has passed from the sound of the alarm till the injection is actually made.

BRIEF SUMMARY OF THE INVENTION

It is an object of the application to provide a syringe by which these problems are overcome.

Another object of the invention is to have the relevant parameters represented electronically in a way which enables presentation of these parameters in any preferred way. When an LCD display is chosen the digits may be arbitrarily large as their size is not dependent on the magnitude of the mechanical movement represented by the displayed parameter. The information may be transformed into sound or Braille and may be transmitted to external displays.

This is obtained by a syringe having a dose setting mechanism, a button operable to carry out an injection movement to inject the set dose, a switch operated at the start or at the completion of the injection, or at a time between the start and the completion of the injection, and an electronic representation of relevant parameters such as of a set dose and latest injected dose, which syringe is according to the invention characterised in that it comprises a stop watch which is reset and started when the switch is operated, the status of the stop watch function being electronically represented.

When the stop watch counts the number of hours passed from the latest operation of the switch, i.e from the latest injection, the user may have a comprehensive view of the time which has passed after the latest injection and the size of this last injection. In this way the user is able to set the next dose with regard to these parameters.

When according to the invention a stop watch is reset and started when the switch is operated, e.g. when the injection movement of the button is completed, the watch is automatically started when an injection is made.

According to an embodiment of the invention, the status of the stop watch immediately after the operation of the switch is displayed in a way indicating the number of seconds passed after said operation. This may guide the user to keep the injection needle inserted for some seconds after the button has been pressed home which is desirable to allow the injected liquid to be adopted in the tissue before the needle is drawn out, as the liquid may else leak out through the wound left by the needle so that a dose minor lower than the intended one is absorbed in the body, and is desirable to allow the full dose to be completely delivered by the syringe. A resting time of 4 to 10 and preferably 6 seconds has been shown to be appropriate.

WO 90/09202 disclosure a syringe in which a timer counts the seconds passing from the beginning of the injection till the injection is completed. This time, however is of less importance and it is recommended that the user himself controls the injection speed as he immediately may feel if the liquid is injected faster than the tissue can absorb it.

According to an embodiment of the syringe according to the invention, the electronic representation of the status of the stop watch is an electronic display on which the status is indicated by segments of which one is activated for each hour passed from the completion of the injection, i.e. after the switch was operated.

During the first seconds of the running of the stop watch the electronic display may be used for guiding the patient to maintain the needle inserted for some seconds after the injection movement of the button has been completed. This guiding is obtained by activating one or more segments per second passing immediately after the completion of the injection movement of the button until all segments of the dial are activated. Thereafter all the segments are deactivated and are reactivated one by one for each hour passing after the switch was operated, i.e. since the latest injection was made.

According to an embodiment of the invention the electronic display may comprise twelve circle segments forming a watch dial and when the segments are activated one per hour passed after the operation of the switch it is done in a sequence so that the segment between the twelve o'clock position and the one o'clock position is activated after one hour, a segment between one o'clock and the two o'clock position is further activated after two hours, and so on.

The same watch dial may conveniently be used to indicate the passage of the first few seconds after the operation of the switch, with the difference that two segments are activated for each second passed after the home pressing of the button. The two segments first activated may e.g. be the segments between the five o'clock and six o'clock position and between the six o'clock and seven o'clock position, the next two segments may be the segments between the seven and eight o'clock and the four and five o'clock positions and so on so that all the segments in the dial are activated during six seconds beginning from the bottom of the dial and spreading clockwise and counter clockwise to the top of the dial. When all the segments have been activated during these first seconds of the running of the stop watch, they are switched off and are then reactivated, one per hour passed since the operation of the switch.

According to an embodiment of the syringe according to the invention said syringe may be equipped with a memory storing data comprising the sizes of a predetermined number of previously injected doses and the time intervals between these doses and the insulin type used by the injections.

BRIEF DESCRIPTION OF DRAWINGS

In the following the invention will be further described with references to the drawing, wherein FIG. 1 shows a display window with none of the display elements activated, FIG. 2 shows the display in FIG. 1 during a test activating all display elements, FIG. 3 shows the display in FIG. 1 showing the size of a set dose, FIG. 4 shows the display in FIG. 1 five seconds after the injection button has been pressed home, FIG. 5 shows the display in FIG. 1 immediately after an injection has been completed, FIG. 6 shows the display in FIG. 1 four hours after the injection of 20 units of a medicine.

DETAILED DESCRIPTION OF THE INVENTION

Figure 7:
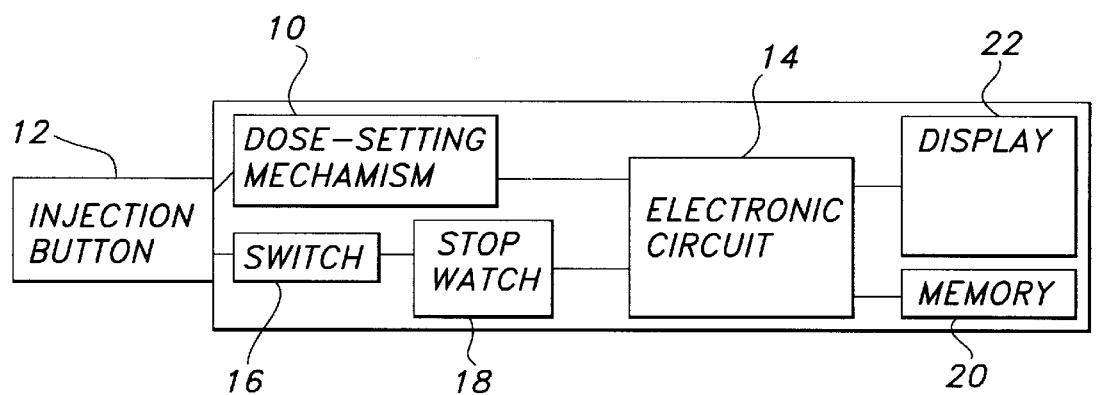
FIG. 7 is a block diagram of a syringe according to the invention.

FIG. 7 depicts schematically a syringe according to the invention which includes a dose setting mechanism 10 and an injection button 12 for carrying out an injection movement to expel the set dose. The dose setting mechanism 10 is coupled to an electronic circuit 14 for communicating the set dose. The injection button 12 is coupled to a switch 16 such that, when the injection button is pressed home, the switch 16 activates a stop watch 18. The stop watch 18 is also coupled to the electronic circuit 14 to provide the elapsed time. The electronic circuit 14 includes a memory 20 and a display 22, which display is described further below.

FIG. 1 shows an embodiment of a display window of a display displaying the electronic representations of parameters such as set dose, latest injected dose, and status of the stop watch according to the invention. None of the display elements are activated. This condition only occurs when the device due to malfunction or expiry is not operative or when the display during storage is switched off to save the battery.

When the device is made ready for use e.g. by removing a protective cap, a short test function may be run by which all the elements of the display are activated to make sure that they work. This condition is shown in FIG. 2. The display elements comprise digits 1 for indication of set doses, segments 2 for indicating time passed, and a dial indicating circle 3 indicating that the hour counting stop watch is running.

When the dose setting mechanism of the syringe is operated, the display changes to the appearance shown in FIG. 3 where the size of the dose set is shown as a number representing the number of units set. As long as the injection is not yet initiated the set dose may be varied.

When the dose is set the needle of the syringe is inserted into the subcutaneous tissue of the user and an injection button is pressed home. When the button is totally pressed home, a switch is activated which switch activates a stop watch counting the hours passing after the completion of said pressing of the button. In the embodiment with the shown display the number of seconds are counted and displayed from the moment when the injection was completed to allow the user to ensure that the needle remains inserted some seconds after the end of the injection is finished. It is recommended to leave the needle in the tissue for 5–10 seconds after the injection is finished to make sure that the full dose has been delivered and that the injected liquid has been distributed in the tissue so that it is not pressed out through the needle wound. FIG. 4 shows the display after five seconds in which two segments of the display are activated per second after the button has been pressed home (which is taken as an indication of the fact that the injection is finished). The activation of the segments starts from the bottom of the dial and progresses by two segments per second one on each side of the dial. The successive activation in FIG. 4 is illustrated by the using a lighter grey tone for the latest activated segments. After six seconds all the segments of the dial are activated and the display now changes to the condition shown in FIG. 5. Here the circle 3 is activated to indicate that the stop watch which counts the hours from the end of the injection is running but, as less than one hour has passed, no segments are activated yet. The reading of the display now indicates the magnitude of the latest injection and the time passed since this injection. FIG. 6 shows the display four hours after 20 units of a medicine were injected.

The first stop watch keeps running until next time the dose setting mechanism is operated. The operation of the dose setting mechanism will change the display to the FIG. 3 appearance, only the display will not show the number "20" but the magnitude of the dose now set When the protective cap is mounted the display is switched off and when the cap is removed the display is switched on. When switched on the display will shortly show the test appearance according to FIG. 2 and then change to the appearance shown in FIG. 6 showing the latest injected dose and the number of hours passed since this injection.

What is claimed is:

1. A syringe comprising:
   a dose-setting mechanism;
   a button operable to carry out an injection movement to inject a set dose;
   a stop watch for measuring elapsed time;
   a switch operated responsive to the injection movement to reset and start the stop watch; and
   an electronic device for communicating relevant parameters to a user including the set dose and the size of the last injected dose; wherein the electronic device includes a display containing a number of segments forming a circle, and activates segments representing the elapsed time, measured by the stop watch, from the last injected dose.

2. A syringe according to claim 1, wherein the display contains twelve segments forming a circle.

3. A syringe according to claim 2, wherein the electronic device activates one segment for each hour which has elapsed after the switch is activated.

4. A syringe according to claim 1, wherein the electronic device, for a predetermined time immediately following activation of the switch, activates at least one segment per second, thereafter deactivates the activated segments, and thereafter activates at least one segment for each hour elapsed.

5. A syringe according to claim 4, wherein the switch is activated at the completion of the injection movement.

6. A syringe according to claim 2, wherein the electronic device, for a predetermined time immediately following activation of the switch, activates at least one segment per second, thereafter deactivates the activated segments, and thereafter activates one segment for each hour elapsed from the activation of the switch.

7. A syringe according to claim 6, wherein the switch is activated at the completion of the injection movement.

8. A syringe according to claim 7, wherein, during said predetermined time, two segments are activated per second.

9. A syringe according to claim 6, wherein the display includes an indicator for indicating that the stop watch is running in its hour-counting mode.

10. A syringe according to claim 9, wherein the indicator is a circle surrounding the segments.

11. A syringe according to claim 1, wherein the display includes a number display for displaying dose information.

12. A syringe according to claim 1, wherein the electronic device includes a memory, and wherein the electronic device stores, and can selectively communicate, the size of a plurality of previously injected doses, the time intervals between the respective doses, and the type of medicament used in the respective doses.

* * * * *

UNITED STATES PATENT AND TRADEMARK OFFICE
CERTIFICATE OF CORRECTION

PATENT NO. : 6,248,090 B1
DATED : June 19, 2001
INVENTOR(S) : Jensen et al.

It is certified that error appears in the above-identified patent and that said Letters Patent is hereby corrected as shown below:

<u>Title page,</u>
Please add
-- Related U.S. Application Data
[63] Continuation of application No. PCT/DK97/00077, February 20, 1997. --

<u>Column 1,</u>
Line 5, change "This application is a 35 U.S.C. 371 national application of" to -- The present application is a continuation of --

<u>Column 2,</u>
Line 30, delete "minor"
Line 35, change "WO 90/09202 disclosure" to -- WO 90/09202 discloses --

Signed and Sealed this

Fifteenth Day of October, 2002

*Attest:*

*Attesting Officer*

JAMES E. ROGAN
*Director of the United States Patent and Trademark Office*